United States Patent [19]

Mori

[11] Patent Number: 5,031,990
[45] Date of Patent: Jul. 16, 1991

[54] LIGHT DISTRIBUTION DEVICE

[76] Inventor: Kei Mori, 3-16-3-501, Kaminoge, Setagaya-ku, Tokyo, Japan

[21] Appl. No.: 456,909

[22] Filed: Dec. 26, 1989

[30] Foreign Application Priority Data

Feb. 3, 1989 [JP] Japan ................................. 1-26076

[51] Int. Cl.$^5$ ............................................. G02B 6/26
[52] U.S. Cl. .................................. 350/96.15; 350/96.10
[58] Field of Search ........................ 350/96.10, 96.15

[56] References Cited

U.S. PATENT DOCUMENTS

| | | | |
|---|---|---|---|
| 4,302,069 | 11/1981 | Niemi | 350/96.18 X |
| 4,447,118 | 5/1984 | Mulkey | 350/96.10 X |
| 4,626,065 | 12/1986 | Mori | 350/96.15 |

Primary Examiner—William L. Sikes
Assistant Examiner—Phan T. Heartney
Attorney, Agent, or Firm—Jordan and Hamburg

[57] ABSTRACT

A light distribution device has a first light-guiding cable for transmitting light rays, a number of second light-guiding cables having light-receiving ends arranged together to form a light-receiving ring plane, a driving means for rotating the light-emitting end of the first light-guiding cable around the light-receiving ring-plane, a light coupler secured at the light-emitting end of the first light-guiding cable. The light coupler has a surface similar to that of a part composing the light-receiving ring-plane of the second light-guiding cables and makes a circular motion along the light-receiving ring-plane at a constant relation thereto.

20 Claims, 4 Drawing Sheets

LIGHT DISTRIBUTION DEVICE

BACKGROUND OF THE INVENTION

The present invention relates to a light distribution device and more particularly to a device which is able to receive light transmitted through a single light-guiding cable and to time-sharingly distribute the same to a large number of light-guiding cables. More concretely, the present invention relates to a device which is capable of effectively supplying light necessary for the photosynthesis of living organisms such as algae, (for example, chlorella, spirulina etc.), photosynthesized bacteria and other artificially photosynthesized substances as for example callus and such living things as plants, mushrooms etc.

A chlorella culturing device, as an example of a photosynthetic reactor, has been proposed in which chlorella is cultured by feeding it with light and carbon dioxide for aiding in the process of photosynthesis. However, as a result of some detailed research into the phtosynthetic process it has been found that one cycle of phtosynthetic reaction in chlorella requires an instant light radiation duration of about 10 microseconds and the rest duration about 200 microseconds therein photosynthetic reaction can be conducted without light radiation, more exactly, the reaction can be more effectively conducted with no light radiation for the rest duration of the cycle. On the other hand, in the case of chlorella culturing it is usual to use such a phtosynthetic reactor (for instance, a chlorella culturing bath) wherein a large number of fluorescent lamps are arranged so as to allow photosynthetic substances to pass through the gaps between the lamps. Said conventional bath, due to the use of a large number of fluorescent lamps, is large and requires the consumption of much electricity. Furthermore it necessitates strong treatment of heat generated by the lamps. To solve these problems, the present applicant has previously proposed that solar rays or artificial rays be focused and introduced into a fiber optic cable and then transmitted therethrough to a light radiator which is used as a light source for a photosynthetic reactor. However, it is also evident that when a large scale photosynthetic reactor is constructed with the use of the above-mentioned light-radiating means, a large number of light radiators must be used or a large-sized device for focusing the sun's rays and/or artificial light rays is necessary.

To solve the above-mentioned problems, the present applicant has also proposed a light distribution device which is able to intermittently supply light energy to photosynthetic substances in order to more effectively promote the process of photosynthesis and therefore is sufficient to cover the need for light energy for any large-scale photosynthetic reactor at the fixed capacity of a solar ray and/or artificial light ray focusing device.

A photosynthetic reactor's light source previously proposed by the present applicant has a light-guiding rod or a light-guiding cable for transmitting solar rays or artificial light rays focused by lenses (not shown) and a transparent rotary rod. The light-emitting end of the light guide is placed opposite the rotating axis of the rotary rod, and a reflecting mirror is provided at the rotating axis of the rotary rod against the light-emitting end of the light guide. The light transmitted through the light guide and introduced into the rotary rod is reflected a the mirror and propagates toward the tip portion of the rotary rod, whereas the light is reflected again by a mirror provided thereat and then radiated out from the light-emitting surface of the rotary rod. A large number of light-guiding rods are arranged to form a ring, placed opposite to the light-emitting surface of the rotary rod. Consequently, when the rotary rod is rotated by a motor, the light-receiving faces of the light-guiding rods to be covered with the light-emitting surface of the rotary rod are changed in turn and each light-guiding rod receives an instant burst of light radiation for each rotation. The end portion of each light-guiding rod serves as a light radiator. The light radiators may be provided at a certain distance from each other in a photosynthetic reactor, or widely spread apart in a plant-cultivating room, a mushroom cultivating place and so on.

As described above, in the light-distribution device provided previously by the present applicant the light delivered thereto through the light guide is supplied momentarily into the light guides and in turn through the rotary rod being rotated and, accordingly, the distributed light is discharged momentarily from the output end of each light-guiding rod, once for each rotation of the rotary rod into a photosynthetic reactor wherein a photosynthetic substance is radiated with the light for a very short period, for instance about 10 microseconds and then initiates a cycle of a photosynthetic reaction and completes the cycle without the need for additional light radiation, and then at the next burst of light radiation, through one rotation of the rotary rod, it initiates a new cycle of photosynthetic reaction. A series of photosynthetic reactions in the reactor is thus continued with periodical light radiation of photosynthetic substances. For initiating the photosynthesis of the object it is necessary to supply no less than a specified amount of light energy. In the above-mentioned light distribution device a necessary amount of light energy may be easily obtained by increasing the density of the light for a very small area corresponding to the light-emitting surface of the rotary rod. Thanks to this construction feature, the device can work well with a compact solar ray or artificial light ray collecting device. Furthermore, since the light discharged from the light-emitting surface of the rotary rod is time-sharingly distributed to many light-guiding rods, the device can supply a sufficient amount of light energy into a photosynthetic reactor of a large capacity.

However, the above-mentioned light distribution device has some drawbacks in that the rotary rod is difficult to make and is expensive.

SUMMARY OF THE INVENTION

In view of the above-mentioned drawbacks of the prior art, it is an object of the present invention to provide a further improved device which is capable of distributing the light transmitted through a single light-guiding cable among a large number of light-guiding cables by applying simpler and lower cost means.

It is another object of the present invention to provide a simple and low cost light distribution device which is capable of evenly and effectively distributing light rays transmitted through a first light-guiding cable to a large number of second light-guiding cables at no additional cost and difficult-to-make light distributing channels.

DESCRIPTION OF THE PREFERRED EMBODIMENTS

Figure 1:
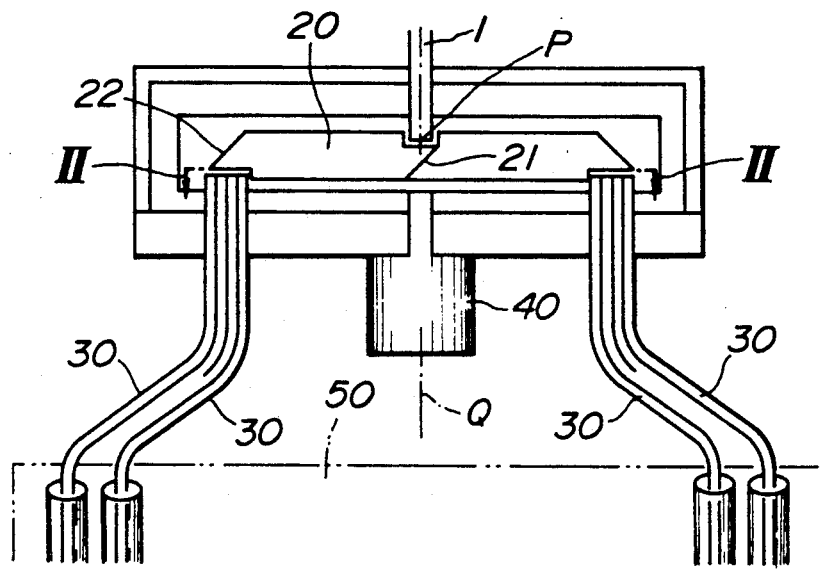
FIGS. 1 and 2 are views for explaining an example of a light distribution device previously proposed by the present applicant.
Figure 2:
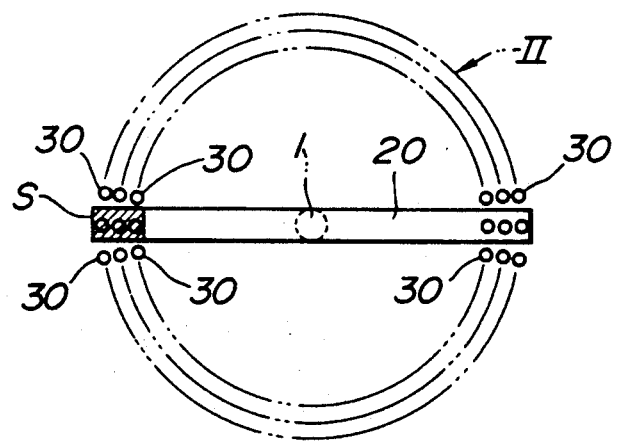

FIG. 1 is a main portion construction view for explaining a photosynthetic reactor's light source previously proposed by the present applicant. In FIG. 1, number 1 designates a light-guiding rod or a light-guiding cable for transmitting solar rays or artificial light rays focused by lenses (not shown) and 20 is transparent rotary rod. The light-emitting end P of the light guide 1 is placed opposite the rotating axis Q of the rotary rod 20, and the reflecting mirror 21 is provided at the rotating axis Q of the rotary rod 20 against the light-emitting end P of the light guide 1. The light transmitted through the light guide 1 and introduced into the rotary rod 20 is reflected at the mirror 21 and propagates toward the tip portion of the rotary rod 20, whereas the light is reflected again by a mirror 22 provided thereat and then radiated out from the light-emitting surface S of the rotary rod 20. A large number of light-guiding rods 30 are arranged to form a ring II, as shown in FIG. 2, placed opposite to the light-emitting surface S of the rotary rod. Consequently, when the rotary rod 20 is rotated by a motor 40, the light-receiving faces of the light-guiding rods 30 to be covered with the light-emitting surface S of the rotary rod 20 are changed in turn and each light-guiding rod 30 receives an instant burst of light radiation for each rotation. The end portion of each light-guiding rod 30 serves as a light radiator. The light radiators may be provided at a certain distance from each other in a photosynthetic reactor or widely spread apart in a plant-cultivating room, a mushroom cultivating place 50 and so on.

As described above, in the light-distribution device, the light delivered thereto through the light guide 1 is supplied momentarily into the light guides 30 and in turn through the rotary rod 20 being rotated and, accordingly, the distributed light is discharged momentarily from the output end of each light-guiding rod 30, once for each rotation of the rotary rod 20 into a photosynthetic reactor wherein a photosynthetic substance is radiated with the light for a very short period, for instance about 10 microseconds and then initiates a cycle of a photosynthetic reaction and completes the cycle without the need for additional light radiation, and then at the next burst of light radiation, through one rotation of the rotary rod 20, it initiates a new cycle of photosynthetic reaction. A series of photosynthetic reactions in the reactor 50 is thus continued with periodical light radiation of photosynthetic substances. For initiating the photosynthesis of the object it is necessary to supply no less than a specified amount of light energy. In the above-mentioned light distribution device a necessary amount of light energy may be easily obtained by increasing the density of the light for a very small area corresponding to the light-emitting surface S of the rotary rod. Thanks to this construction feature, the device can work well with a compact solar ray or artificial light ray collecting device (not shown). Furthermore, since the light discharged from the light-emitting surface S of the rotary rod 20 is time-sharingly distributed to many light-guiding rods 30, the device can supply a sufficient amount of light energy into a photosynthetic reactor of a large capacity.

However, the above-mentioned light distribution device has some drawbacks in that the rotary rod 20 is difficult to make and is expensive.

In view of the above-mentioned drawbacks of the prior art, the present invention was made in order to provide a further improved device which is capable of distributing the light transmitted through a single light-guiding cable among a large number of light-guiding cables by applying simpler and lower cost means.

Figure 3:
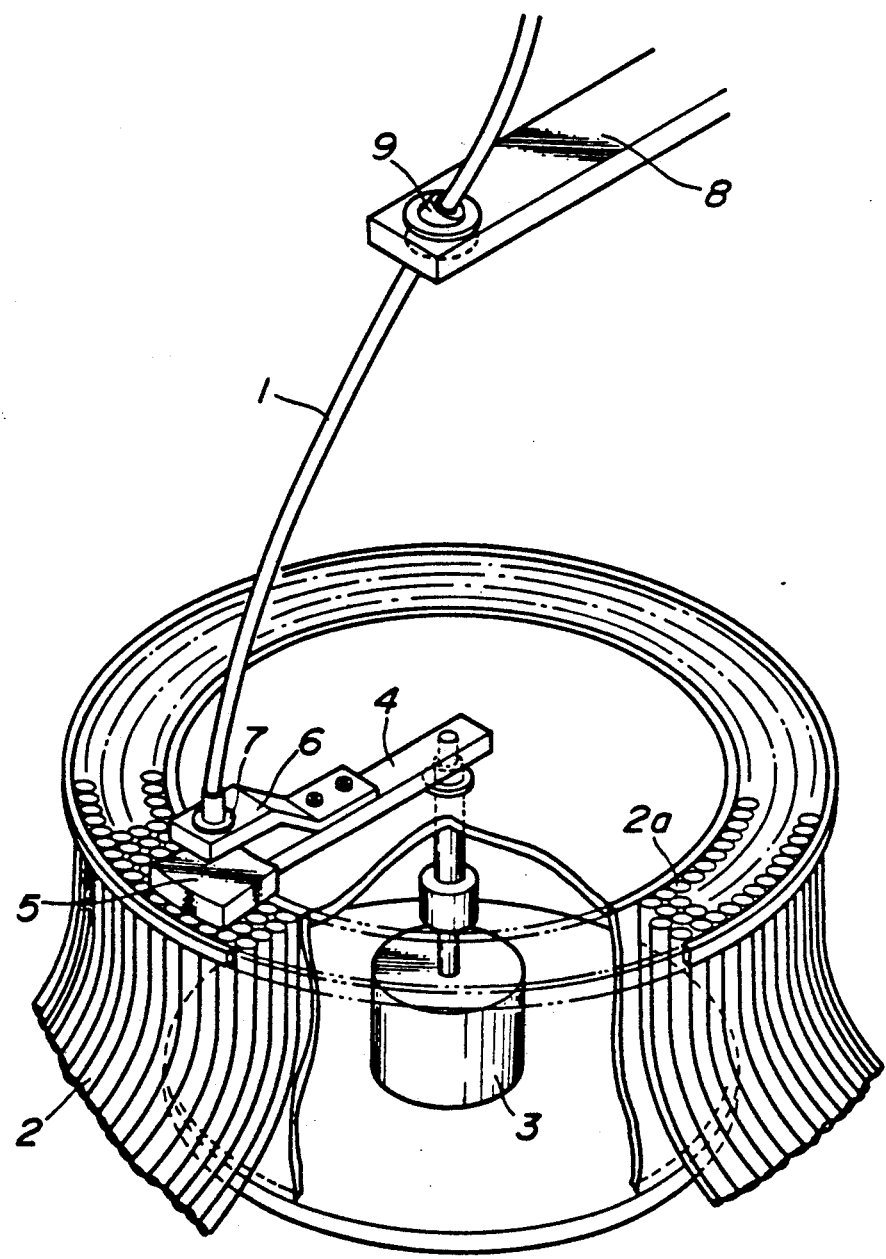
FIG. 3 is a construction view for explaining an embodiment of the present invention.

FIG. 3 is a construction view for explaining a preferred embodiment of the present invention. In FIG. 3, numeral 1 designates a first single light-guiding cable for transmitting solar rays or artificial light rays introduced into its light-receiving end (not shown) and numeral 2 designates a large number of secondary light-guiding cables, light-receiving ends 2a which are arranged together to form a ring of a light-receiving plane. An arm 4, to be rotated by a motor 3 has at its front end a light-coupler 5 secured thereto and also an auxiliary arm 6 secured thereto for holding the light-emitting end of the first light-guiding cable 1 by loosely fitting said cable's end in a bearing 7 provided at said auxiliary arm 4. An arm 8 supports the end portion of the light-guiding cable 1 by loosely inserting said cable's end through a spherical bearing provided in its front end, preferably being aligned with the axis of the driving motor. Accordingly, when the motor 3 rotates in the state shown in FIG. 3, the arm 4 is rotated to move the light coupler 5 and the light-emitting end of the light-guiding cable 1 along the ring-plane formed by the light-emitting ends of a large number of light-guiding cables 2 and, thereby, to realized the sequential distribution of the light to the light-guiding cables 2 in the same way as the above-described prior art. In the embodiment of the present invention, the light-guiding cable 1 can be rotated as it is being supported in the spherical bearing 9 that eliminates the possibility of damage to said cable due to excessive force. While in the described case the spherical bearing 9 supports the rotating axis of the guide cable 1, it is also possible to support the cable only in a loose hole of the arm without using the spherical bearing. However, in such a case there may be fear of damaging the outer surface of the cable 1 due to the possible rubbing of said surface against the inner surface of the through-hole. In the same manner, the light-emitting end of the light-guiding cable 1 can be loosely fitted in a through-hole of the auxiliary arm without using a supporting bearing 7. In both cases the light-emitting end of the light-guiding cable 1 can be rotated without being twisted along the ring-plane formed by the light-emitting faces 2a of a large number of the light guide cables 2.

Figure 4:
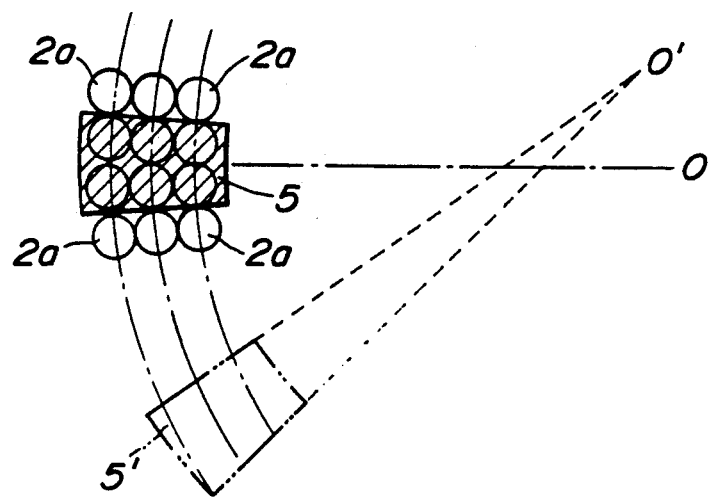
FIG. 4 is a plane view showing the relationship between a light coupler and the light-receiving face of the light-guiding cable.
Figure 5A:
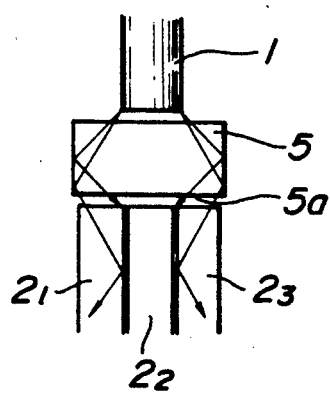
FIG. 5(a) is a side view showing the relationship between the light-emitting end of the light guide cable, the light coupler and the light-receiving face of the light-guiding cable.
Figure 5B:
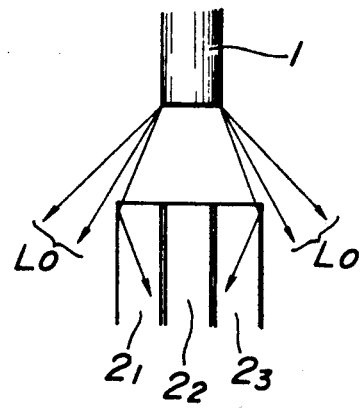
FIG. 5(b) is a side view showing a case when the coupler is omitted in FIG. 5(a)

FIGS. 4 and 5 are views for explaining the relationship between the light-emitting end of a light-guiding cable 1, the light coupler 5 and the light-guiding cables 2. FIG. 4 is a plane view showing the relationship between the light coupler 5 and the light-receiving face 2a of the light-guiding cables 2, FIG. 5(a) is a side view showing the relationship between the light-emitting end of the light-guiding cable 1, the light-coupler 5 and the light-receiving face of the light-guiding cable 2 and FIG. 5(b) is a side view showing the case when the coupler 5 is omitted in FIG. 5(a). In the embodiment shown in FIG. 5(a), the light emitted from the light-guiding cable 1 is introduced into the light coupler 5 wherein said light is reflected by the side walls thereof and is guided into the light-guiding cables 2. Furthermore, the relationship between the light coupler 5 and the light-receiving face of the light-guiding cables 2 is kept constant. In other words, the rotating axis of the light coupler 5 and the axis of the ring formed by the light-receiving faces of the light-guiding cables coincide with each other at a common center (O). It is possible that the relationship of the light coupler 5 relative to the ring-plane as shown by a broken line in FIG. 4 may not happen, i.e. no displacement of the axis of the light coupler 5 to the point (O') occurs. The light rays emitted from the light-guiding cable 1 are introduced into the light coupler 5 and then reflected by the side walls to form a light beam of an almost uniform density which is then discharged through the output end 5a of the light coupler 5. Consequently, each of the light-guiding cables 2 can receive a substantially equal amount of the light. This means that an equal amount of light can be obtained when any of the light-guiding cables 2 is chosen. On the contrary, if the light coupler 5 is omitted, scattered light rays Lo to the side, as shown in FIG. 5(b), cannot be guided into the light-guiding cables 2 and a light beam emitted from the light-guiding cable 1 may be different in strength at its end portions, namely, the strength of said light beam may be reduced gradually from the center portion to the periphery. Consequently, in the case shown in FIG. 5(b), an amount of light introduced into each of the light-guiding cables $2_1$ and $2_3$ is smaller than that of the light-guiding cable $2_2$. Accordingly, the amount of light depends upon which is chosen among the light-guiding cables 2. To prevent the light-guiding cable 1 from being twisted, its light-emitting end may freely rotated on a bearing of the light coupler 5. So, if said coupler 5 is omitted, the light-guiding cable 1 may be twisted and hence an amount of the light introduced into the light-guiding cables 2 becomes unstable. Such a light distribution device should not be used in the case when an optimum or given amount of light is needed.

Figure 6:
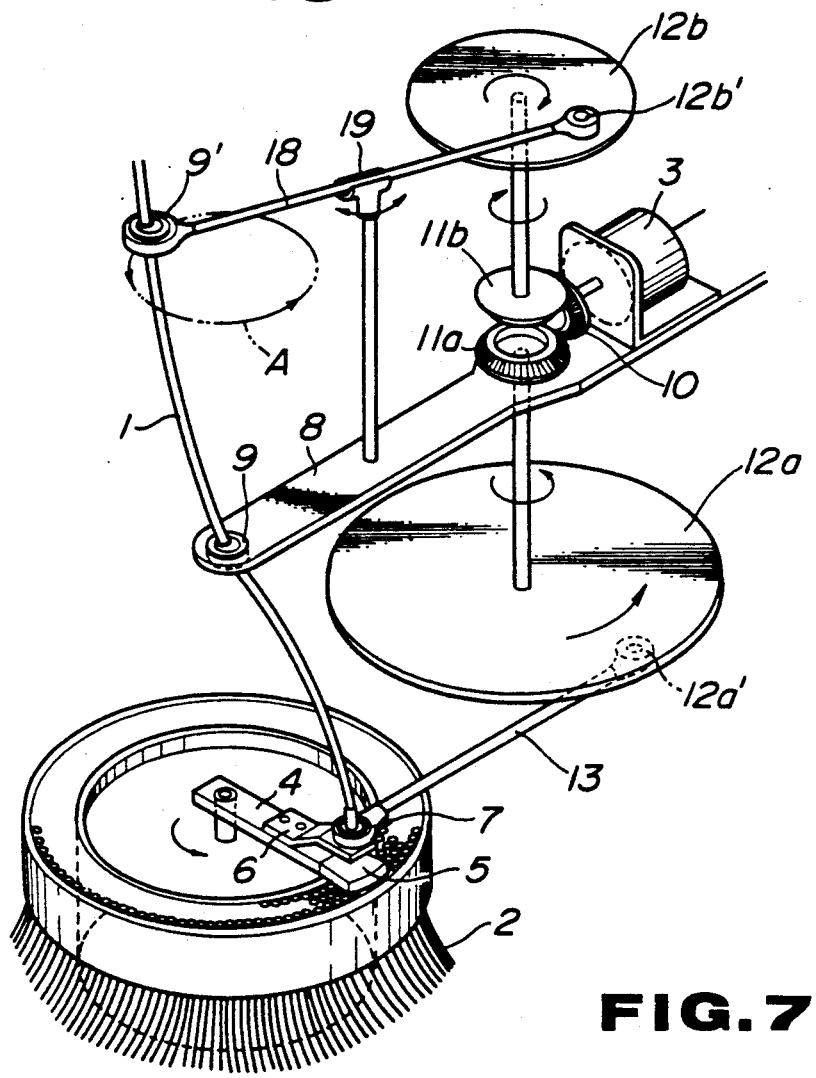
FIG. 6 is a construction view for explaining another embodiment of the present invention.
Figure 7:
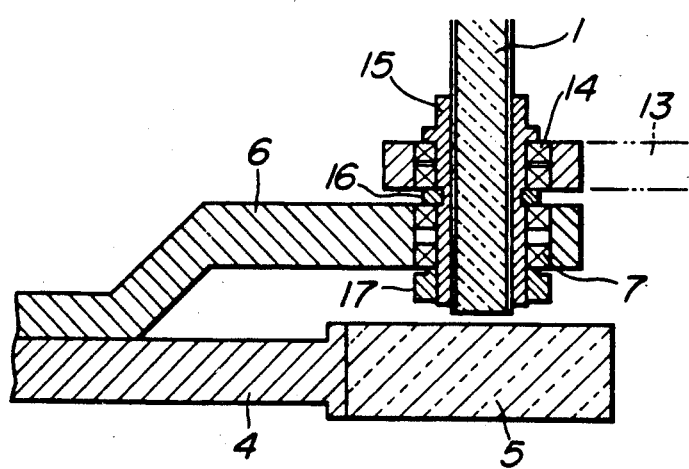
FIG. 7 is an enlarged detailed view for explaining an example of a coupling for an end portion of a driving arm shown in FIG. 6 with a light-guiding cable.

FIG. 6 is a construction view for explaining another embodiment of the present invention. In FIG. 6, 1 is a first light-guiding cable, 2 is a second light-guiding cables, 3 is a motor, 4 is an arm, 5 is a light coupler, 6 is an auxiliary arm, 7 is a bearing, 8 is a support arm and 9 is a spherical bearing. Since these elements are similar in their function to those of the embodiment described with reference to FIG. 3, the detailed description is omitted. In FIG. 6, a beveled gear 10 is driven from the motor 3 and its rotation is transmitted to other bevel gears 11a and 11b. A rotary disc 12a is mounted on the rotating axis of the bevel gear 11a and a driving arm 13 has one end rotatably fitted onto a projecting pin 12a' eccentrically disposed at the rotary disc 12 and the other end rotatably fitted onto the light-emitting end of the light-guiding cable 1. As shown in detail in FIG. 7, the other end of the driving arm 13 is rotatably secured at the light-guiding cable 1 by means of a bearing 14 in order to rotate the light coupler 5 along a ring-plane formed by the light-receiving faces of the light-guiding cables 2. In FIG. 7, 15 is a collar fitted onto the light-emitting end of the light-guiding cable 1, 16 is a spacer for separating the bearing portions 7 and 14 from each other, 17 is an element for supporting the bearing 7. On the other hand, the rotation of the bevel gear 11b is transmitted to another disc 12b where a pin 12b' is eccentrically disposed for rotatably fitting one end of the arm 18 thereto. Said arm 18 has a spherical bearing 9' (identical to the bearing 9) at the other end, for loosely fitting through the light-guiding cable 1. 19 is a supporting element for supporting the arm 18 by its upper end which is rotatable in the direction shown by the arrow. Accordingly, when the disc 12b is rotated, the tip end of the arm 18 makes a circular motion as shown by an assumed circle A. This circular motion A is made in the same direction as the movement of the light coupler 5 and is 180°, out of phase with respect to the circular motion of the light coupler 5. In the embodiment of the present invention, the tip end of the light-guiding cable 1 (the light coupler 5) makes a spinning motion around the axis of the bearing 9. The circular motion of the bearing 9 assists the free spinning motion of the tip end of the light-guiding cable 1 by reducing the load applied thereto. While in the above mentioned arrangement the single arms 13 and 18 are used for the purpose of simplifying the explanation, it may be easily understood that other driving means, for instance, parallel-linked mechanisms and the like are also applicable in the devices according to the present invention.

As is apparent from the foregoing description, according to the present invention, it may be possible to provide a simple and low cost light distribution device which is capable of evenly and effectively distributing light rays transmitted through a first light-guiding cable to a large number of second light-guiding cables at no additional cost and difficult-to-make light distributing channels.

I claim:
1. A light distribution apparatus comprising:
   a first light-guide cable for transmitting light rays, said first light-guide cable having an end portion having a light emitting end;
   a plurality of second light-guide cables each having an end portion having a light receiving end;
   support means for supporting said end portions of said second light-guide cables in a generally circular array about a central axis with each of said light receiving ends being disposed in a light receiving ring plane; and
   revolving means for revolving said end portion of said first light-guide cable over said light receiving ring plane, said revolving means carrying a light coupler means disposed at said light emitting end of said first light-guide cable such that when said light emitting end of said first light-guide cable passes over said light receiving ring plane, the light rays are transmitted from said light emitting end through said coupler means to said light receiving ends of said second light-guide cables, said light coupler means having a light receiving surface juxtaposed to said light emitting end of said first light-guide cable and a light emitting surface juxtaposed to said light receiving ring plane.

2. A light distribution apparatus according to claim 1, wherein said light coupler means has side surfaces extending between said light receiving surface and said light emitting surface, said side surface being reflective surfaces.

3. A light distribution apparatus according to claim 1, wherein said light coupler means has side surfaces extending between said light receiving surface and said light emitting surface, said side surfaces being clad surfaces.

4. A light distribution apparatus comprising:
a first light-guide cable for transmitting light rays, said first light-guide cable having an end portion having a light emitting end;
a plurality of second light-guide cables each having an end portion having a light receiving end;
support means for supporting said end portions of said second light-guide cables in a generally circular array about a central axis with each of said light receiving ends being disposed in a light receiving ring plane having the configuration of an annulus; and
revolving means for revolving said end portion of said first light-guide cable over said light receiving ring plane, said revolving means carrying a light coupler means disposed at said light emitting end of said first light-guide cable such that when said light emitting end of said first light-guide cable passes over said light receiving ring plane, the light rays transmitted from said light emitting end through said coupler means to said light receiving ends of said second light-guide cables, said coupler means having an overall configuration of a sector of said annulus.

5. A light distribution apparatus comprising:
a first light-guide cable for transmitting light rays, said first light-guide cable having an end portion having a light emitting end;
a plurality of second light-guide cables each having an end portion having a light receiving end;
support means for supporting said end portions of said second light-guide cables in a generally circular array about a central axis with each of said light receiving ends being disposed in a light receiving ring plane, said light receiving ring plane having an outer diameter spaced from an inner diameter; and
revolving means for revolving said end portion of said first light-guide cable over said light receiving ring plane, said revolving means carrying a light coupler means disposed at said light emitting end of said first light-guide cable such that when said light emitting end of said first light-guide cable passes over said light receiving ring plane, the light rays are transmitted from said light emitting end through said coupler means to said light receiving ends of said second light-guide cables, said coupler means having an outer circular wall having a diameter substantially equal to said outer diameter of said light receiving ring plane, said coupler means having an inner circular wall having a diameter substantially equal to said inner diameter of said light receiving ring plane.

6. A light distribution apparatus according to claim 5, wherein said coupler means has spaced side walls each disposed in an axial plane which includes said central axis.

7. A light distribution apparatus comprising:
a first light-guide cable for transmitting light rays, said first light guide cable having an end portion having a light emitting end;
a plurality of second light-guide cables each having an end portion having a light receiving end;
support means for supporting said end portions of said second light-guide cables in a generally circular array about a central axis with each of said light receiving ends being disposed in a light receiving ring plane; and
revolving means for revolving said end portion of said first light-guide cable over said light receiving ring plane, said revolving means carrying a light coupler means disposed at said light emitting end of said first light-guide cable such that when said light emitting end of said first light-guide cable passes over said light receiving ring plane, the light rays are transmitted from said light receiving ends of said second light-guide cables, said revolving means comprising a main arm which supports said coupler means, and an auxiliary arm extending from said main arm for supporting said end portion of said first light-guide cable.

8. A light distribution apparatus comprising:
a first light-guide cable for transmitting light rays, said first light-guide cable having an end portion having a light emitting end;
a plurality of second light-guide cables each having an end portion having a light receiving end;
support means for supporting said end portions of said second light-guide cables in a generally circular array about a central axis with each of said light receiving ends being disposed in a light receiving ring plane; and
revolving means for revolving said end portion of said first light-guide cable over said light receiving ring plane, said revolving means carrying a light coupler means disposed at said light emitting end of said first light-guide cable such that when said light emitting end of said first light-guide cable passes over said light receiving ring plane, the light rays are transmitted from said light emitting end through said coupler means to said light receiving ends of said second light-guide cables, said revolving means comprising a revolving arm supporting one part of said first light-guide cable and a stationary arm supporting another part of said first light-guide cable.

9. A light distribution apparatus according to claim 8 further comprising a rotary bearing on said revolving arm for rotatably supporting said one part of said first light-guide cable.

10. A light distribution apparatus according to claim 8 further comprising a spherical bearing for supporting said other part of said first light-guide cable or said stationary arm.

11. A light distribution apparatus according to claim 10, wherein said spherical bearing has a center which is coincident with said central axis.

12. A light distribution apparatus comprising:
a first light-guide cable for transmitting light rays, said first light-guide cable having an end portion having a light emitting end;
a plurality of second light-guide cables each having an end portion having a light receiving end;
support means for supporting said end portions of said second light-guide cables in a generally circular array about a central axis with each of said light receiving ends being disposed in a light receiving ring plane; and revolving means for revolving said end portion of said first light-guide cable over said light receiving ring plane, said revolving means carrying a light coupler means disposed at said light emitting end of said first light-guide cable such that when said light emitting end of said first light-guide cable passes over said light receiving ring plane, the light rays are transmitted from said light emitting end through said coupler means to said light receiving ends of said second light-guide cables, said revolving means comprising motor means having a drive shaft, said revolving means further comprising a linkage means between said drive shaft and said end portion of said first light-guide cable, said drive shaft having an axis coincident with said central axis.

13. A light distribution apparatus comprising:

a first light-guide cable for transmitting light rays, said first light-guide cable having an end portion having a light emitting end;

a plurality of second light-guide cables each having an end portion having a light receiving end;

support means for supporting said end portions of said second light-guide cables in a generally circular array about a central axis with each of said light receiving ends being disposed in a light receiving ring plane; and revolving means for revolving said end portion of said first light-guide cable over said light receiving ring plane, said revolving means carrying a light coupler means disposed at said light emitting end of said first light-guide cable such that when said light emitting end of said first light-guide cable passes over said light receiving ring plane, the light rays are transmitted from said light emitting end through said coupler means to said light receiving ends of said second light-guide cables, said revolving means comprising a motor means, first linkage means between said motor means and one part of said first light-guide cable for revolving said first part over said light receiving ring plane, second linkage means between said motor means and a second part of said first light-guide cable for revolving said second part about a circle, said one part of said first light-guide cable being axially spaced from said second part of said first light-guide cable.

14. A light distribution apparatus according to claim 13, wherein said first linkage means comprises a first link arm rotatably connected to said first part of said first light-guide cable, a first driven shaft driven by said motor means, and a first eccentric connection between said first driven shaft and said first link arm.

15. A light distribution apparatus according to claim 14, wherein said second linkage means comprises a second link arm rotatably connected to said second part of said first light-guide cable, a second driven shaft driven by said motor means, and a second eccentric connection between said second driven shaft and said second link arm.

16. A light distribution apparatus according to claim 15, wherein said first and second driven shafts having aligned axes.

17. A light distribution apparatus according to claim 15, wherein said first and second eccentric connections are 180 degrees out of phase with one another.

18. A light distribution apparatus according to claim 13, wherein said revolving means further comprises a fixed mounting means having a mounting arm, and bearing means rotatably mounting said mounting arm on a third part of said first light-guide cable, said third part being axially intermediate said one and said second parts.

19. A light distribution apparatus according to claim 18, wherein said motor means is mounted on said mounting means.

20. A light distribution apparatus according to claim 13, wherein said second link arm has an intermediate section, said mounting means having a support rod for supporting said intermediate section of said second link arm.

* * * * *